US012682456B2

(12) United States Patent
Beriault et al.

(10) Patent No.: US 12,682,456 B2
(45) Date of Patent: Jul. 14, 2026

(54) QUALITY OF IMAGES FOR RADIOTHERAPY

(71) Applicant: Elekta, Inc., Atlanta, GA (US)

(72) Inventors: Silvain Beriault, Longueuil (CA); Laurence Savard, Crawley (GB)

(73) Assignee: Elekta, Inc., Atlanta, GA (US)

( * ) Notice: Subject to any disclaimer, the term of this patent is extended or adjusted under 35 U.S.C. 154(b) by 343 days.

(21) Appl. No.: 18/473,638

(22) Filed: Sep. 25, 2023

(65) Prior Publication Data

US 2024/0112332 A1 Apr. 4, 2024

(30) Foreign Application Priority Data

Sep. 28, 2022 (GB) ...................................... 2214195

(51) Int. Cl.
*G06T 7/00* (2017.01)
*G16H 30/20* (2018.01)

(52) U.S. Cl.
CPC ........... *G06T 7/0012* (2013.01); *G16H 30/20* (2018.01); *G06T 2207/30168* (2013.01)

(58) Field of Classification Search
CPC ........ G06T 7/0012; G06T 2207/30168; G16H 30/20; A61N 5/1064; A61N 5/1067; A61N 2005/1054; A61N 2005/1055; A61N 2005/1061; A61N 5/1049; A61N 5/1068; A61N 5/1048; A61N 5/1065; A61B 6/52; A61B 6/5264; A61B 6/527
See application file for complete search history.

(56) References Cited

U.S. PATENT DOCUMENTS

| | | | | |
|---|---|---|---|---|
| 9,248,316 B2 * | 2/2016 | Lachaine | ............. | A61N 5/1049 |
| 2007/0041494 A1 | 2/2007 | Ruchala et al. | | |
| 2011/0160589 A1 | 6/2011 | Fu et al. | | |
| 2016/0225132 A1 | 8/2016 | Han et al. | | |
| 2016/0324500 A1 * | 11/2016 | Fan | ........................ | A61B 5/055 |
| 2018/0193674 A1 | 7/2018 | Brooks | | |
| 2022/0001210 A1 | 1/2022 | Letourneau et al. | | |
| 2024/0112332 A1 * | 4/2024 | Beriault | ............. | A61N 5/1049 |

FOREIGN PATENT DOCUMENTS

WO WO-2023279188 A1 1/2023

OTHER PUBLICATIONS

"European Application Serial No. 23199531.7, European Search Report dated Feb. 14, 2024", (Feb. 14, 2024), 7 pgs.
"United Kingdom Application No. 2214195.6, Search and Examination Report dated Mar. 13, 2023", (Mar. 13, 2023), 6 pgs.

* cited by examiner

*Primary Examiner* — Darryl V Dottin

(74) *Attorney, Agent, or Firm* — Schwegman Lundberg & Woessner, P.A.

(57) ABSTRACT

A computer-implemented image evaluation method for a radiotherapy device, a radiotherapy device and a computer-readable medium are provided. The computer-implemented image-evaluation method comprises obtaining a time series of images of a subject disposed in the radiotherapy device. The computer-implemented image-evaluation method further comprises determining a quality factor for an image of the time series of images. The computer-implemented image-evaluation method further comprises, in response to determining that the quality factor does not meet a condition, generating a computer-executable instruction for adjusting operation of the radiotherapy device.

19 Claims, 7 Drawing Sheets

700

710

QUALITY OF IMAGES FOR RADIOTHERAPY

CLAIM FOR PRIORITY

This application claims the benefit of priority of British Application Serial No. 2214195.6, filed Sep. 28, 2022, which is hereby incorporated by reference in its entirety.

TECHNICAL FIELD

This disclosure relates to radiotherapy, and in particular to determining a quality factor for images of a subject disposed in a radiotherapy device.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In radiotherapy treatment, it is desirable to deliver a prescribed dose of radiation to a target region of a subject and to limit irradiation of other parts of the subject, i.e. of healthy tissue. Motion of the subject can cause a decreased dose to be applied to the target region and/or an increased dose to be applied to the healthy tissue. To address this, known techniques include monitoring a location of the subject and gating the treatment beam such that radiation is applied only when the subject (i.e. the target region within the subject) is in a desired location and not when the subject/target region is in a suboptimal location. Doing so ensures that the dose actually delivered to the target and surrounding healthy tissue best corresponds to the intended treatment plan typically defined on a static planning image with a no-motion assumption.

There are various physiological motions that can contribute to a total motion of a subject. Discrete, gross or large-scale movements of a subject may include shifting position, coughing or sneezing. The subject may also undergo cyclical, physiological movement. For example, the subject may undergo respiratory motion due to their breathing cycle. The subject may also undergo cardiac motion based on beating of their heart. The subject may also undergo non-periodic (e.g. drifting) motion. For example, bladder filling may cause the prostate to drift in position. These motions can alter the location of a subject and/or of a tumour in a time-dependent manner relative to the respective location of the subject and/or of the tumour at the start of the radiotherapy treatment.

Application of radiation by the radiation source in some time periods but not in others may be achieved by gating of a radiation beam emitted by the radiation source. The radiation source may comprise an electron source and a radiofrequency (RF) field source. The electron source may provide a source of electrons which generate a radiation dose to be delivered to the subject, for example by impacting a target. The RF field source may electromagnetically accelerate the electrons to a desired velocity suitable for providing the radiation dose. The radiation source may be gated by controlling the electron source to be on or off and/or by controlling the RF field source to be on or off. In this manner, application of a radiation dose by the radiation source can be controlled according to desired parameters.

During a gated radiotherapy delivery, images may be obtained for monitoring the motion of the subject or parts of the subject. Based on these images, an indication of the previous, current or predicted position and motion trajectory of the subject or parts of the subject can be derived. However, algorithms used to determine the position or motion trajectory may give inaccurate outputs depending on the images that are input to the algorithms. This can be due to changes in motion pattern that may occur during the treatment or due to known limitations of the algorithms. The output of the algorithms can be used to determine where the target is, for example whether the target is in a location suitable for applying radiotherapy to the target. Basing radiotherapy treatment on inaccurate outputs may lead to application of unsuitably high dose to healthy patient tissue or unsuitably low dose to a tumour, which may negatively affect patient outcomes from radiotherapy treatment sessions.

SUMMARY

A computer-implemented image evaluation method for a radiotherapy device, may comprise: obtaining a time series of images of a subject disposed in the radiotherapy device; determining a quality factor for an image of the time series of images; and in response to determining that the quality factor does not meet a condition, generating a computer-executable instruction for adjusting operation of the radiotherapy device.

A radiotherapy device may comprise a radiation source configured to apply a radiation beam; an imaging apparatus; and a controller communicatively coupled to the radiation source and the imaging apparatus, the controller being configured to: obtain a time series of images of a subject disposed in the radiotherapy device; determine a quality factor for an image of the time series of images; and in response to determining that the quality factor does not meet a condition, generate a computer-executable instruction for adjusting operation of the radiotherapy device.

A non-transitory computer-readable medium may include instructions which, when executed by a processor of a computing device, cause the processor to perform the above-mentioned method.

BRIEF DESCRIPTION OF THE DRAWINGS

Specific embodiments are now described, by way of example only, with reference to the drawings, in which.

DETAILED DESCRIPTION

Figure 1:
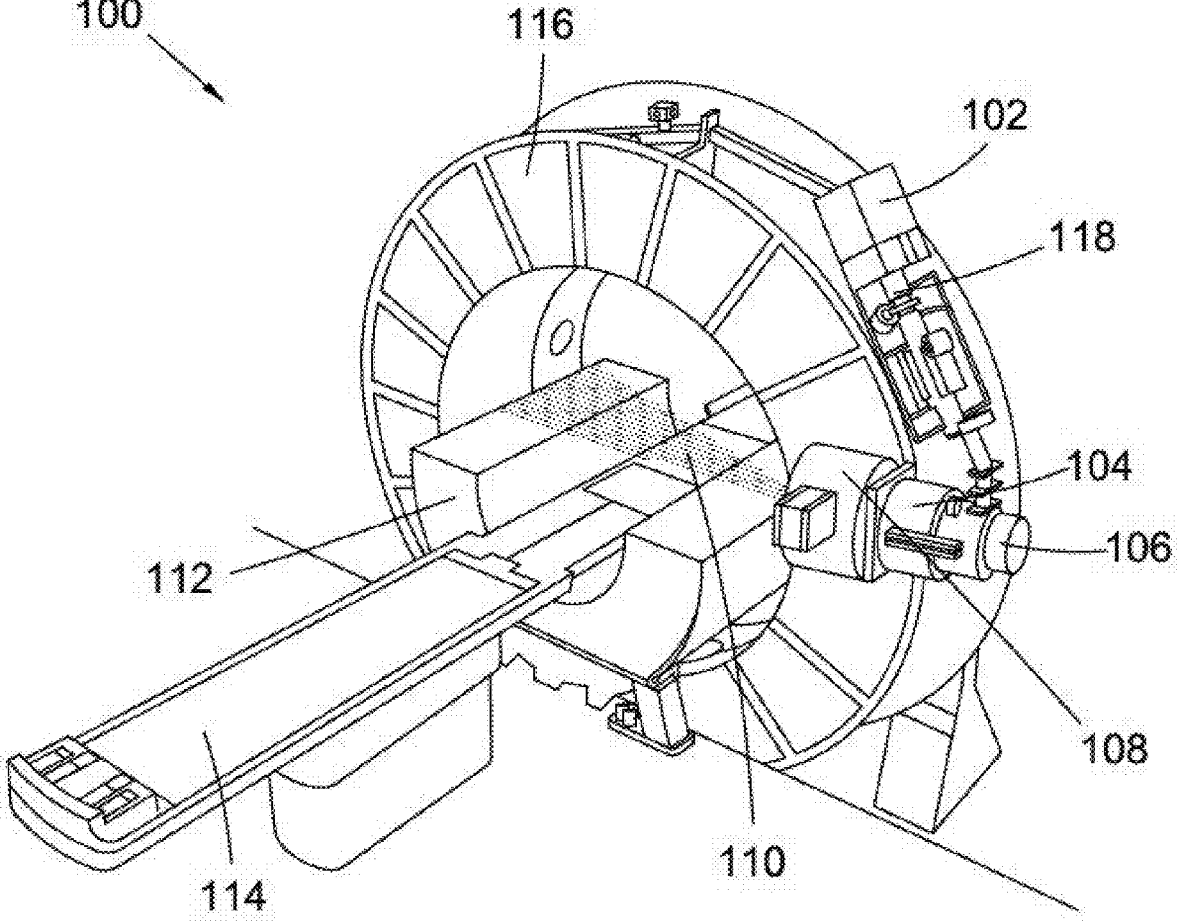
FIG. 1 depicts a radiotherapy device or apparatus according to the present disclosure.

During a gated delivery, a time series of images may be acquired for motion-monitoring purposes. Based on these images, an anatomical position monitoring (APM) target trajectory signal can be derived. This can be used to estimate the 3D displacement of a tumour of the subject. However, the motion tracking algorithm used for APM can return inaccurate motion estimates depending on the images that are input. This can be due to changes in motion pattern that may occur during the treatment or due to known limitations of the tracking algorithm. For example, abnormally large deformations can be particularly challenging to detect using optimisation-based registration because a larger search-space is required, which increases the risk that the algorithm gets trapped in a wrong local minimum. As another example, large through-plane motion can pose challenges since the motion is estimated from a single 2D image plane and some anatomical features enter or exit the plane. As a further example, temporal jitter may occur when translation estimates are performed on interleaved coronal and sagittal images that can exhibit different anatomical features. Therefore, there are properties of the input images that can be identified as likely to lead to inaccurate motion estimation.

The present disclosure provides techniques for evaluating image quality for a radiotherapy device. In particular, these images may be for input to an anatomical position monitoring algorithm. According to the present disclosure, a computer-implemented method involves obtaining a time series of images of a subject disposed in a radiotherapy device. The images of the time series may, for example, be two-dimensional (2D) MR (magnetic resonance) images or 2D kilo voltage (kV) images. A quality factor for at least one image of the time series of images is determined. This quality factor can be determined by determining one or more quality metrics, each of the quality metrics being associated with a different respective property of the image, which can be aggregated to determine the quality factor. For example, the respective quality metrics can indicate whether there is a large deformation associated with the image, whether the image indicates large through-plane motion, the degree of subject motion during breath-hold treatments, the amount of jitter associated with the image and previous images, the change in image intensity of the image relative to previous images, and/or one or more other properties of the image.

The determined quality factor is compared to a condition, which can be used to indicate whether or not the image is suitable for inputting to an anatomical position monitoring algorithm to provide an accurate output. In response to determining that the quality factor does not meet the condition, a computer-executable instruction for adjusting operation of the radiotherapy device is generated. For example, delivery of a radiation beam can be stopped or prevented. This avoids the risk of radiating a subject based on inaccurate indications of their movement or anatomical position which could otherwise occur based on use of input images which have not been checked or evaluated.

FIG. 1 depicts a radiotherapy device suitable for delivering, and configured to deliver, a beam of radiation to a patient during radiotherapy treatment. The device and its constituent components will be described generally for the purpose of providing useful accompanying information for the present disclosure. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation 106, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller. As used herein, a controller may also be referred to as a control device.

The RT apparatus comprises a source of radiation and a radiation detector (not shown). Typically, the radiation detector is positioned diametrically opposed to the radiation source. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation is configured to direct a beam 110 of therapeutic radiation toward a patient positioned on the patient support surface 114. The source of radiation may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move to different positions including a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by one or more subject support surface actuators, which may be described as an actuation mechanism. The actuation mechanism is configured to move the subject support surface at least in a direction parallel to, and defined by, the central axis of the bore. The terms subject and patient are used interchangeably herein such that the patient support surface can also be described as a subject support surface. The subject support surface may also be referred to as a moveable or adjustable couch or table or as a patient couch or subject couch.

The radiotherapy apparatus/device depicted in FIG. 1 also comprises MR imaging apparatus 112. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller. While the discussion herein may focus on MR imaging by way of example, alternatively or in addition to MR imaging, one or more other imaging techniques, modalities, sensors or detectors may be used, such as CT/X-ray, PET, optical imaging/cameras, infra-red imaging, ultra-sound imaging or time-of-flight techniques. Any one or more of these may be used to generate images of the subject and/or to determine the position of the target.

The controller is a computer, processor, or other processing apparatus. The controller may be formed by several discrete processors; for example, the controller may comprise a processor for each of the various individual components of the radiotherapy device as described herein. The controller is communicatively coupled to a memory, e.g. a computer readable medium. The controller may be communicatively coupled to one, multiple or all of the various individual components of the radiotherapy device as described herein. As used herein, the controller may also be referred to as a control device.

The linac device also comprises several other components and systems as will be understood by the skilled person. For example, in order to ensure the linac does not leak radiation, appropriate shielding is also provided.

The radiotherapy device and/or the control device may be configured to perform any of the method steps presently disclosed and may comprise computer executable instructions which, when executed by a processor cause the processor to perform any of the method steps presently disclosed, or when executed by the control device cause the control device to perform any of the method steps presently disclosed, or when executed by the radiotherapy device cause the radiotherapy device to perform any of the method steps presently disclosed. Any of the steps that the radiotherapy device and/or the control device is configured to perform may be considered as method steps of the present disclosure and may be embodied in computer executable instructions for execution by a processor. A computer-readable medium may comprise the above-described computer executable instructions.

Referring to FIG. 1, axes may be defined as follows. The z-axis may be defined as pointing into/out of the bore of the gantry 116 and concentric with the gantry 116. The x-axis may be defined as pointing horizontally left/right relative to the centre of the bore. The y-axis may be defined as pointing vertically up/down relative to the centre of the bore.

Anatomical positions within a subject are typically defined by reference to coronal, sagittal and transverse planes. The coronal plane divides the body into front and back portions. The sagittal plane divides the body into left and right portions. The transverse plane divides the body into head and tail portions. For a subject lying on the patient support surface 114 of FIG. 1, the coronal plane is defined in the x-z plane relative to the radiotherapy device. Similarly, the sagittal plane is defined in the y-z plane. The transverse plane is defined in the x-y plane relative to the radiotherapy device.

During a radiotherapy treatment, it may not be practical to acquire full 3D information on positions of anatomical features of the subject because the time associated with acquisition and processing of such information may lead to longer than desired latency, which would prevent the derived positions being capable of serving as 'real-time' information for informing whether to adjust machine or treatment parameters. Instead, a series of 2D image slices may be obtained and used to determine, estimate or infer the positions of anatomical positions of the subject, for example through comparing to 3D reference data obtained before treatment began. For example, image acquisition may alternate between generating 2D coronal and sagittal images, i.e. 2D images in the coronal and sagittal planes respectively. Since these planes intersect, positions of anatomical features of the subject, relative to their pre-treatment positions, can be inferred. In other examples, multiple sagittal slices may be acquired with different depths to create a sparse 3D volume.

A treatment plan for a subject may comprise information specifying the radiotherapy machine parameters to be used for treating the subject. This is based on the subject being disposed in a particular position within or relative to the radiotherapy device. For example, this may be based on one or more pre-treatment or template images of the subject. These machine parameters may be optimised for delivering a particular radiative dose to the anatomical position of the target (tumour) within the subject and avoiding delivering substantial dose to healthy tissue within the subject. However, during a radiotherapy treatment session, the subject or parts of the subject may move, for example due to breathing, cardiac motion, coughing, twitching, etc. Images of the subject may be generated during the treatment session in order to provide a real-time, or close to real-time, check on the position of the subject or parts of the subject. This can be used to determine whether/when the subject is in a suitable position for delivering radiation to the target. The beam may be gated on when the subject is in a suitable position and gated off when the subject is not in a suitable position.

An algorithm may be used to determine the position of the subject or parts thereof from the images. As used herein, this will be referred to as an anatomical position monitoring (APM) algorithm. By way of illustration, an APM algorithm using 2D MR images will be referred to below, though it will be appreciated that other imaging modalities may be used to monitor the position of the subject or parts thereof. During a gated delivery, 2D MR images of the subject may be acquired for motion-monitoring purposes. Based on these images, an APM target trajectory signal may be determined, which may estimate the positions of anatomical positions of the subject as a function of time relative to one or more static template images, for example by comparing the anatomical positions of the features in the different images. Different methods may be used for estimating the target trajectory signal on 2D MR images. One possible embodiment includes the use of optimization-based registration or each image in the 2D MR image series to a template (reference) image. Another possible embodiment includes the use of machine learning regression methods.

A coronal image provides information in the x and z dimensions. When a coronal image is obtained, it can be compared to a static template image for the coronal plane, which may be obtained pre-treatment and may be registered to a 3D reference. This can be used to determine the movement of anatomical features of the subject relative to the template image in the x and z dimensions. In other words, this provides dx and dz components of the subject motion.

A sagittal image provides information in the y and z dimensions. When a sagittal image is obtained, it can be compared to a static template image for the sagittal plane, which may be obtained pre-treatment and may be registered to the 3D reference. This can be used to determine the movement of anatomical features of the subject relative to the template image in the y and z dimensions. In other words, this provides dy and dz components of the subject motion.

Based on the above, it will be appreciated that the APM algorithm can provide estimates for position changes/movements in two out of the three dimensions for each frame. When a coronal image is processed, dx and dz components are updated. When a sagittal image is processed, dy and dz components are updated. For each frame, the APM algorithm may output dx, dy and dz components. However, while the dz component may be updated every frame, the dx and dy components may be updated every other frame in an interleaved manner. This is because acquisition of images in coronal and sagittal planes is alternated, i.e. the time series of images obtained may comprise alternating coronal and sagittal images. While this explanation has been provided in respect of alternating between acquisitions in the coronal and sagittal planes, it will be appreciated that corresponding processing could be performed by alternating between acquisitions in the coronal and transverse planes or by alternating between acquisitions in the sagittal and transverse planes.

The accuracy of the motion estimates returned by the APM algorithm may depend on the images that are input. This can be due to changes in motion pattern that may occur during the treatment or due to known limitations of the APM algorithm. Since the outputs of the APM algorithm may be used to monitor and adjust treatment, it would be advantageous to identify input images for which inaccurate output images are likely to result and to prevent these from negatively affecting treatment. The present disclosure provides techniques for determining and utilising a quality factor for the input images in order to address this need.

The quality factor described herein may be implemented as the aggregation of multiple quality metrics each designed to detect a specific problematic feature in the input images. Some of these metrics may be image-based in that they are applied to one or more of the raw input images themselves. Some of these metrics may be transform-based metrics in that they are applied to the output of the APM algorithm, i.e. to the transform describing the (dx, dy, dz) movement of anatomical features of the subject relative to the template image.

The image-based metrics may be independent from the estimated transform. They can therefore be run in parallel to the APM algorithm, which can avoid increasing latency associated with providing the output positions, especially if these metric can be calculated on the GPU (graphics processing unit) or a different CPU (central processing unit) processor in parallel to the APM algorithm. Even though the APM algorithm could appear to produce an acceptable tracking result, an image-based metric could indicate that one or more input images are of low quality and unsuitable for providing accurate outputs. These image-based metrics therefore add redundancy and safety to the APM algorithm by detecting images that could be problematic for the APM algorithm.

The transform-based metrics may be applied to the estimated APM transform and therefore run after the APM algorithm has provided its output. They provide additional quality checks/quality assurance on the estimated transform to identify potential issues with the APM output retroactively. However, these issues with the APM output may ultimately be considered a result of properties of the images that are input to the APM algorithm.

Therefore, the quality factor described herein provides or comprises an indication of whether or not one or more input images are suitable for estimating positions of anatomical features of the subject (e.g. using an APM algorithm), for example within a predetermined margin or level of accuracy. As used herein, the quality factor of an image may be described as a quality of the image. The quality factor may be an aggregation of one or more of the quality metrics described below.

In some examples, a large deformation quality metric may be determined. This aims to detect large deformations of anatomical features of an image relative to corresponding anatomical features of a template image. Since this metric is determined based on a raw input image, it is may be described as an image-based metric.

Figure 2A:
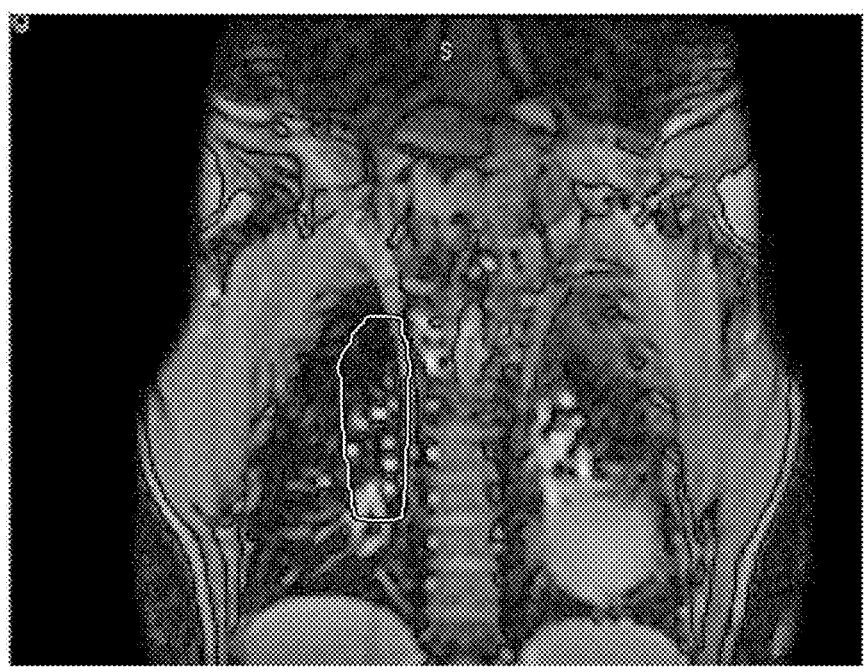
FIGS. 2a-b, 3a-c and 4a-b depict example images according to the present disclosure.
Figure 2B:
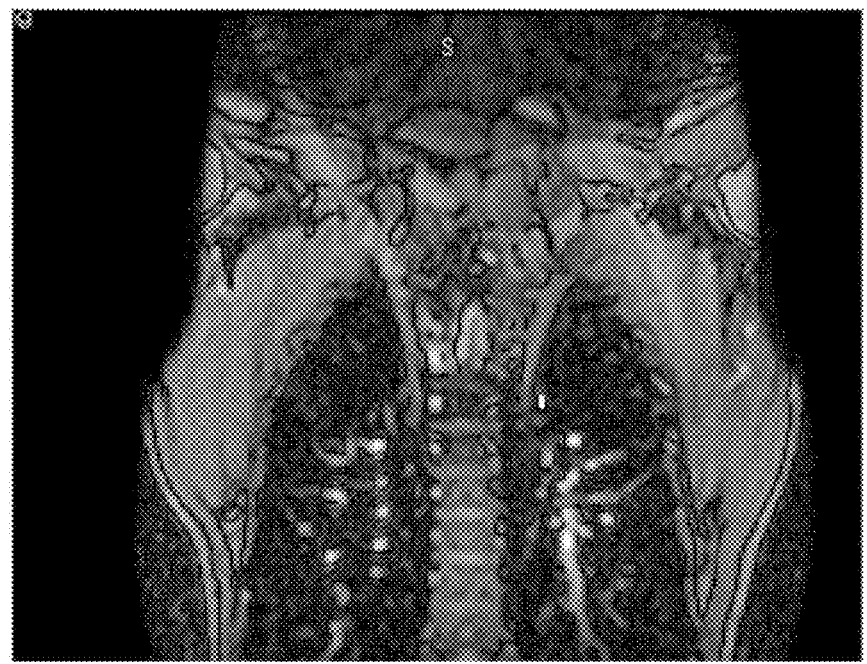

FIG. 2a depicts an example image according to the present disclosure. A tracked region is outlined in grey slightly to the left of centre of the image. FIG. 2b depicts a further example image according to the present disclosure. FIG. 2b is an image later in the same time series that includes FIG. 2a. In FIG. 2b, the anatomy of the subject has moved significantly in a downward direction. This large deformation may make it difficult to estimate the position of the tracked region accurately. To demonstrate this, the tracked region is no longer outlined in FIG. 2b since its location is uncertain.

For a large deformation of subject anatomy, determining the transform using optimisation-based registration can be challenging for the APM algorithm because a larger search-space is required, which increases the risk that the algorithm gets trapped in a wrong local minimum. Moreover, the rigid target motion assumption posed by many APM algorithm implementations may no longer hold, i.e. different anatomical features may stretch or move to different extents relative to each other. As such, an estimated displacement of subject anatomy relative to a template image determined by the APM may be inaccurate for input images exhibiting large deformations. In recognition of this, an input image may be analysed to determine if it exhibits an abnormally large deformation.

Machine learning techniques may be used to determine whether an image indicates a large deformation in one or more anatomical features. A deformable image registration (DIR) algorithm may be used to compute a displacement vector field (DVF) between an input image and the template. Advantageously, the deformable registration algorithm can run on a GPU in parallel to the APM algorithm without adding any significant latencies. As opposed to the APM algorithm, the DVF may be computed on the whole image (and not just the tracked region) in order to capture global (rather than local) deformation features.

In order to determine which DVFs should be classified as corresponding to a large deformation, a principal component analysis (PCA) may be performed over all DVFs estimated during a preparation (training) phase. During treatment, abnormally large motion may be detected by measuring the absolute difference $\text{diff}_i$ between the first principal component of the image ($\text{PCA}_{im\_i}$) and the first principal component of a 'zero-motion' DVF—a DVF where all pixels are at $(0,0,0)$ ($\text{PCA}_{zero\_motion}$):

$$\text{diff}_i = \text{abs}(\text{PCA}_{im\_i} - \text{PCA}_{zero\_motion})$$

The average and standard deviation of this difference may be calculated over N training images (where N is an integer) and then used to determine a decision threshold. In some examples, N may be equal to 60. In some examples, the training images can be the first N images of the image series. In some other examples, the training images can be the last N images to precede the current image sample. In some other examples, the training images can be any combination images that preceded the current image sample. The threshold may represent a subcondition for this quality metric. In order words, this quality metric may be considered not to meet the subcondition if the deformation exceeds this threshold. The image may be considered to be 'high quality' in respect of this quality metric if the deformation does not exceed the threshold and 'low quality' in respect of this quality metric if the deformation does exceed the threshold. In some examples, a different threshold may be used for high→low quality transitions to that used for low→high quality transitions. For example, the following form of threshold may be used:

$$\text{threshold} = \begin{cases} \mu_{diff} + 2.5 * \sigma_{diff} & \text{High} \to \text{Low transition} \\ \mu_{diff} + 2.0 * \sigma_{diff} & \text{Low} \to \text{High transition} \end{cases}$$

The use of these two different thresholds prevents oscillation between high and low quality determinations, which may otherwise occur if the deformation is close to a (single) threshold.

In some examples, a through-plane motion quality metric may be determined. This aims to detect movement of subject anatomy into/out of the acquisition frame perpendicular to the plane of the image. This may be determined by comparing the size of the registration mask (i.e. the tracked target) before and after applying the transform (translation) estimated by the APM algorithm. Since this metric is determined based on the determined transform, it may be considered a transform-based metric.

Figure 3A:
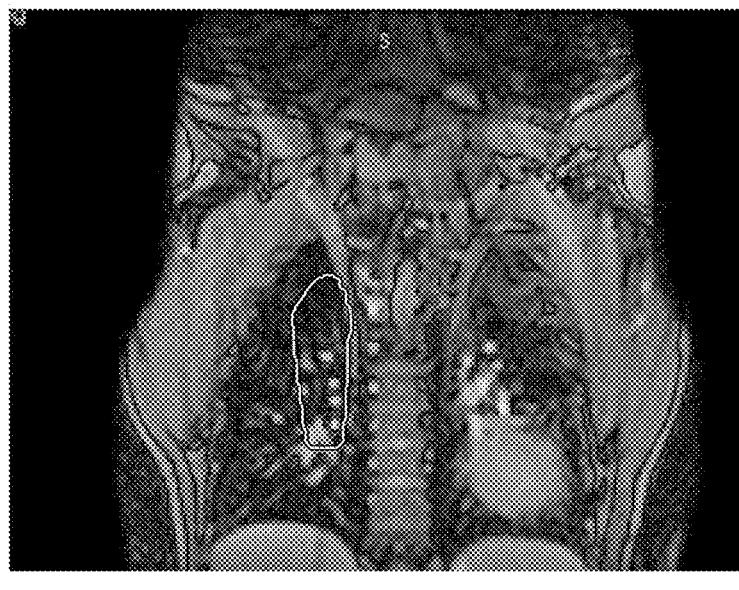
Figure 3B:
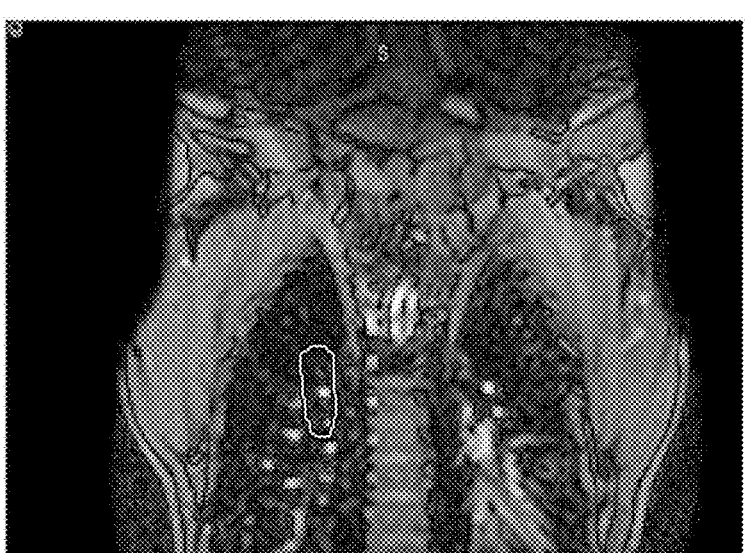
Figure 3C:
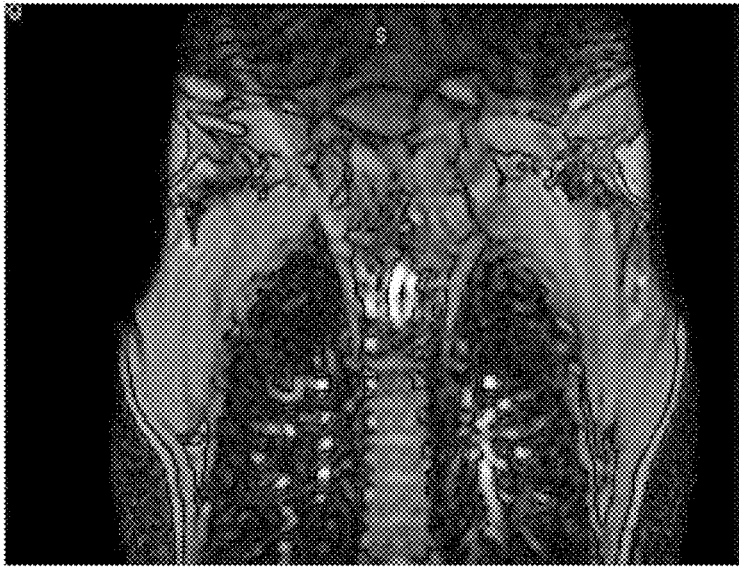

FIG. 3a depicts an example image according to the present disclosure. A tracked region is outlined in grey slightly to the left of centre of the image. FIG. 3b depicts a further example image according to the present disclosure. FIG. 3b is an image later in the same time series that includes FIG. 3a. In FIG. 3b, the anatomy of the subject has moved significantly perpendicular to the image acquisition plane. As a result, the tracked region outlined in grey has become smaller. This is because the area of intersection of the tracked region with the image acquisition plane has decreased in size. FIG. 3c depicts a further example image according to the present disclosure. FIG. 3c is an image later in the same time series that includes FIG. 3a and FIG. 3b. In FIG. 3c, even more through-plane motion has occurred such that the tracked region does not intersect the image acquisition plane. As a result, there is no tracked region outlined in grey in FIG. 3c. The large through-plane motion depicted in these images may make it difficult to estimate the position of the tracked region accurately.

In order to determine whether large through-plane motion has occurred, a ratio between the size of the registration mask (capturing/corresponding to the tracked region) before and after applying the estimated translation may be calculated:

$$ratio = \frac{\int_{slice} mask \circ T}{\int_{slice} mask \circ I},$$

where mask∘T is the mask transformed by the transform T estimated by the APM algorithm and mask∘I is the mask before the transformation (I here means the identity matrix, meaning the mask is in the reference position). $\int_{slice}(\cdot)$ indicates the 2D area of the 3D registration mask once intersected by the acquisition slice (i.e. the sum of all pixels inside the mask on the 2D acquisition slice). If the ratio is less than 1, through-plane motion is determined to be causing the tracked anatomy to shrink in size. An image may be determined to be 'low quality' if the ratio is smaller than a threshold and to be 'high quality' otherwise. For example, the threshold may be set to 0.2, i.e. indicating a registration mask 20% of its original area. If the ratio is greater than 1, through-plane motion is determined to be causing the tracked anatomy to increase in size. In this situation, the ratio may be inverted and the same threshold explained above (or a different ratio) may be applied.

In some examples, a jitter quality metric may be determined. This aims to detect variation in transform estimates in respect of different frames/images. Since this metric is determined based on the determined transforms, it may be considered a transform-based metric.

As explained above, when a coronal image is processed, dx and dz components are updated. When a sagittal image is processed, dy and dz components are updated. For each frame, the APM algorithm may output dx, dy and dz components. The dz component may be updated every frame, but the dx and dy components may be updated every other frame in an interleaved manner. Temporal jitter in the APM transform estimates can occur along the superior-inferior dimension (i.e. the z-axis) because this component of the transform is estimated for both coronal and sagittal images, which can exhibit very different image content and therefore lead to different estimates for the z component of the transform.

In order to detect the presence of jitter, the average jitter observed over the last N frames (where N is an integer) may be determined. In some examples, N may be equal to 5. The jitter J may be calculated as:

$$J = \frac{\sum_{i=2}^{N-1} abs\left(T_z[i] - \left(\frac{T_z[i-1] + T_z[i+1]}{2}\right)\right)}{N-2}$$

$T_z[i]$ represent the z component of the estimated APM transform at index i in the aforementioned window of the last N frames. Similarly, $T_z[i-1]$ and $T_z[i+1]$ correspond to the z component of the estimated APM transform before and after frame i. Since coronal and sagittal images are interleaved, frames i−1 and i+1 have the same image orientation and opposite image orientation to frame i. The term $$\left(\frac{T_z[i-1] + T_z[i+1]}{2}\right)$$

is the linear interpolation of $T_z[i-1]$ and $T_z[i+1]$. The summation term $$\sum_{i=2}^{N-1}$$

indicates that each estimated z-translation ($T_z$) at index i is compared to the linearly interpolated $T_z$ at index i−1 and i+1 (i.e. the $T_z$ values estimated using the other acquisition plane). First and last frames are excluded from the summation since there is either no frame i−1 or no frame i+1 available. An image may be determined to be 'low quality' if the jitter is above a threshold and 'high quality' otherwise. For example, a threshold of J>5 mm may be used for transitioning from high to low quality and a threshold of J<4 mm may be used for transitioning from low to high quality. The use of these two different thresholds prevents oscillation between high and low quality determinations, which may otherwise occur if the jitter is close to a (single) threshold.

In some examples, the treatment is delivered when the subject is holding their breath with deep inspiration. In such a case, tracking errors can occur during the recovery phase since the images are far from the template. As such, it may be important to consider the state of breathing of the subject when determining the suitability of input images to produce accurate APM algorithm outputs.

To address this issue, in some examples, an "absence of motion" quality metric may be determined to detect if the subject is holding their breath or recovering. This aims to detect whether there is a change in images across many consecutive frames, i.e. whether or not the subject is holding their breath. This metric is appropriate for applying to breath-hold treatments in which the subject holds their breath for a significant amount of time. Since this metric is determined based on raw input images, it may be considered an image-based metric.

An image and one or more other images of the time series of images may be compared to determine presence or absence of motion of the subject. In order to determine this, a normalised cross-correlation (NCC) may be computed within the registration mask between the current image and the N previous images (where N is an integer) of the same orientation. The quality metric may be determined as the minimum NCC value over all the N frames. In an example, N may be equal to 5, which is suitable for detecting 'no motion' sequences longer than 2 seconds (assuming interleaved coronal/sagittal images acquired at a 5 Hz frequency). The NCC may be computed as follows:

$$NCC = \sum_{x,y} \frac{1}{\sigma_f \sigma_t}(f_{x,y} - \bar{f})(t_{x,y} - \bar{t}),$$

where f and t are the two images to compare, x and y are the pixel indices and $\bar{f}$, $\bar{t}$, $\sigma_f$ and $\sigma_t$ are the mean and standard deviations over all pixels in the mask. During preparation/ training, the minimum NCC may be computed for each preparation image frame and independently on sagittal and coronal orientations. A NCC threshold is determined using a sufficiently large number of preparation images containing both breath-hold and respiratory frame examples. An appropriate threshold may be set, for example by running the Jenks clustering algorithm, which seeks to determine the best arrangement of values (i.e. calculated NCC values) into different classes (i.e. breath-hold vs respiratory classes) by seeking to minimize each class's average deviation from the class mean, while maximizing each class's deviation from the means of the other classes. An image may be determined to be 'low quality' if the motion is above the threshold and 'high quality' otherwise.

In some examples, a drop in registration score quality metric may be determined. This metric is appropriate for applying to breath-hold treatments that may require tracking larger subject motion since the registration template is typically created in deep inspiration. As such, the APM algorithm is more likely to get trapped in a wrong local minimum. This metric aims to determine whether the estimated transform converged to a strong local minimum. This metric may be considered a transform-based metric since it depends on the APM tracking results.

In an example, the normalised cross-correlation may be computed (inside the registration mask) between an image and the template using the estimated transform (i.e. the output of the APM algorithm). To determine if the estimated APM transform correspond to a strong minimum, the NCC is calculated using different transforms within a 5×5 mm window centred around the estimated transform (i.e. around the output of the APM algorithm). A 'low quality' may be determined when the NCC drops by more than 10%, with a 'high quality' determined otherwise.

In some examples, an intensity change quality metric may be determined. This aims to detect a sudden change in intensity indicating a global change in contrast. Since this metric is determined based on raw input images, it may be considered an image-based metric.

Figure 4A:
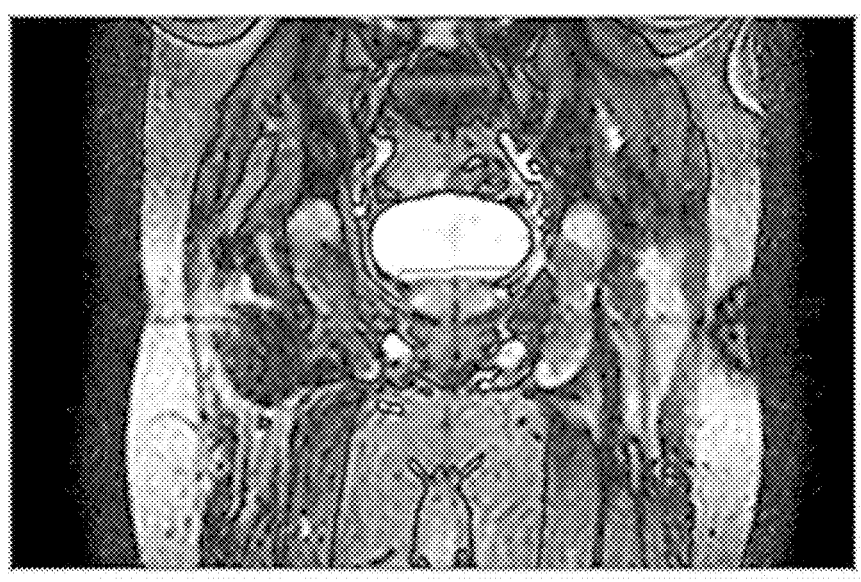
Figure 4B:

FIG. 4a depicts an example image according to the present disclosure. FIG. 4b depicts a further example image according to the present disclosure. FIG. 4b is an image later in the same time series that includes FIG. 4a. In FIG. 4b, the intensity of the image has decreased significantly. This can be problematic if a fast registration metric such as 'sum of squared difference' (SSD) is used, and may make it difficult to identify corresponding anatomical features in different images and therefore difficult estimate the position of the tracked region accurately.

In order to detect a global intensity change, the Earth Mover's Distance (EMD) between a histogram of the input image and an average histogram averaged over the first N images (where N is an integer) may be calculated. In an example, N may be equal to 60. The Earth Mover's Distance is a measure of the distance between two probability distributions over a region. If the EMD is above a threshold, the image may be determined to be 'low quality', with the image being determined to be 'high quality' otherwise. This quality metric can be calculated on the entire image or a sub-region of the entire image.

Determining the quality factor as described herein may comprise determining a quality metric, with the quality metric being considered to be the quality factor. Determining the quality factor as described herein may comprise determining a plurality of quality metrics, each of the quality metrics being associated with a different respective property of the image as described above. Any combination/subset of the above-mentioned quality metrics, or other quality metrics, may be used. Determining the quality factor may comprise aggregating the quality metrics. Determining that the quality factor meets a condition may comprise determining that each of the quality metrics considered meets a respective subcondition, e.g. whether the quality metric indicated high or low quality of the image.

The quality factor of an image may be determined to be 'high quality'. A high quality may indicate that the image is suitable for estimating a position of anatomical features of the subject (e.g. to a predetermined level of accuracy), for example using the APM algorithm. A high quality may indicate that the quality factor meets a condition. This may indicate that each considered quality metric meets a subcondition, i.e. that each applied quality metric returned a 'high quality' result. The quality factor may be determined to be high quality if all quality metrics applied were high quality, and to be low quality otherwise. In other examples, the quality factor may be considered to be high quality if all but one, all but two, etc. quality metrics applied were high quality.

The quality factor of an may be determined to be 'low quality'. A low quality may indicate that the image is not suitable for estimating a position of anatomical features of the subject (e.g. to a predetermined level of accuracy), for example using the APM algorithm. A low quality may indicate that the quality factor does not meet a condition. This may indicate that one or more considered quality metrics did not meet a subcondition, i.e. that one or more quality metric returns a 'low quality' result. The quality factor may be determined to be low quality if any quality metrics applied were low quality. In other examples, the quality factor may still be considered to be 'high quality' if a small number (e.g. only one or two) of the quality metrics was determined to be low quality.

The quality factor of an image may be determined to be 'unknown'. This may indicate that the quality factor was not evaluated, or not evaluated successfully. The quality factor of an image may be determined to be 'not ready'. This may indicate that the quality factor has not yet been (fully) determined or that the determination of the quality factor is in a preparation/training phase.

As described herein, the quality factor may be compared to a threshold and/or quality metrics may be compared to respective thresholds to determine high or low quality/ whether a condition or subcondition is met. These thresholds may be the same, or may be different between different metrics/between metrics and the quality factor. The thresholds may be determined using a training process configured to determine what thresholds would be appropriate to retain/ remove an appropriate number of images, e.g. to minimise the number of false negatives and false positives determined.

In some examples, a respective quality factor may be determined for each of two or more consecutive frames. An overall quality factor for the two or more consecutive frames may only be determined to be high quality if all the quality factors (e.g. all the considered quality metrics for all the respective quality factors) are determined to be high quality. This may advantageously avoid high quality→low quality→high quality→low quality oscillations, which could otherwise lead to disrupted, stop-start treatment instructions.

While aggregation based on high/low quality indications has been described above, the current disclosure is not limited thereto. For example, the quality factor and/or one or more of the quality metrics may take the form of a score, grade or numerical value. For example, each of the quality metrics may be determined in the form of a respective number normalised to one, with a quality metric of one indicating the highest possible level of suitability for inputting to the APM algorithm. Each of the quality metrics may be averaged to determine the quality factor. The quality factor may be compared to a numerical threshold (e.g. a decimal between 0 and 1) to determine whether it meets the condition and whether a computer-executable instruction for adjusting operation of a radiotherapy device should be generated.

The quality metrics that are included in the determination of the quality factor may be determined based on a type of treatment, for example as indicated in a treatment plan. This advantageously enables more targeted application of metrics and limits false positives and false negatives through applying only those quality metrics that are likely to be of relevance for a particular treatment type. Different combinations of metrics may be used for different treatment types (e.g. respiratory, breath-hold, non-respiratory). For example, the metrics used may be as specified in Table 1 below. The deformation detection metric may be most suitable for respiratory motion. For breath-hold and non-respiratory motion, the range of acceptable PCA coefficients may be harder to estimate from preparation images since motion is very limited on those frames. The metrics that detect absence of motion and drops in registration scores may advantageously be applied for the breath-hold workflow.

TABLE 1

Combination of metrics that may be used for different motion types.

| Motion Type | Deformation | Jitter | Through-plane | No motion | Registration score |
|---|---|---|---|---|---|
| Respiratory | Enabled | Enabled | Enabled | Disabled | Disabled |
| Breath-hold | Disabled | Enabled | Enabled | Enabled | Enabled |
| Non-respiratory | Disabled | Enabled | Enabled | Disabled | Disabled |

In response to determining that the quality factor for an image does not meet a condition, one or more computer-executable instructions may be generated for adjusting operation of the radiotherapy device. Each of the one or more computer-executable instructions may be transmitted to a respective component of the radiotherapy device, which may implement the respective computer-executable instruction to adjust operation of the radiotherapy device.

In some examples, the computer-executable instruction may be to halt or prevent application of a radiotherapy beam, i.e. to gate the beam. The beam may be gated even if the APM algorithm determines that the target is within a window indicating that treatment should be applied. This avoids the risk of applying dose to anatomical locations where it should not be applied based on inaccurate transform estimations resulting from input images that are difficult for the APM algorithm to process accurately.

In some examples, the computer-executable instruction may be to reduce an intensity of the radiation beam in order to lower the dose applied. This may allow a treatment to continue, thereby increasing the efficiency of radiotherapy treatment, but with a lower dose such that moderate positional inaccuracies do not lead to unacceptable dose to healthy tissue. For example, this may be applied when the quality factor only just fails to meet the condition (e.g. only one quality metric fails to meet a subcondition, the numerical quality factor is within a preset range or percentage of a numerical threshold, etc.), or only one or a small number of images have quality factors which fail to meet the condition. Alternatively or in addition, in some examples, the computer-executable instruction(s) may be configured to slow down treatment, for example by reducing the speed of rotation of the gantry 116 such that treatment is advanced more slowly.

Figure 5:
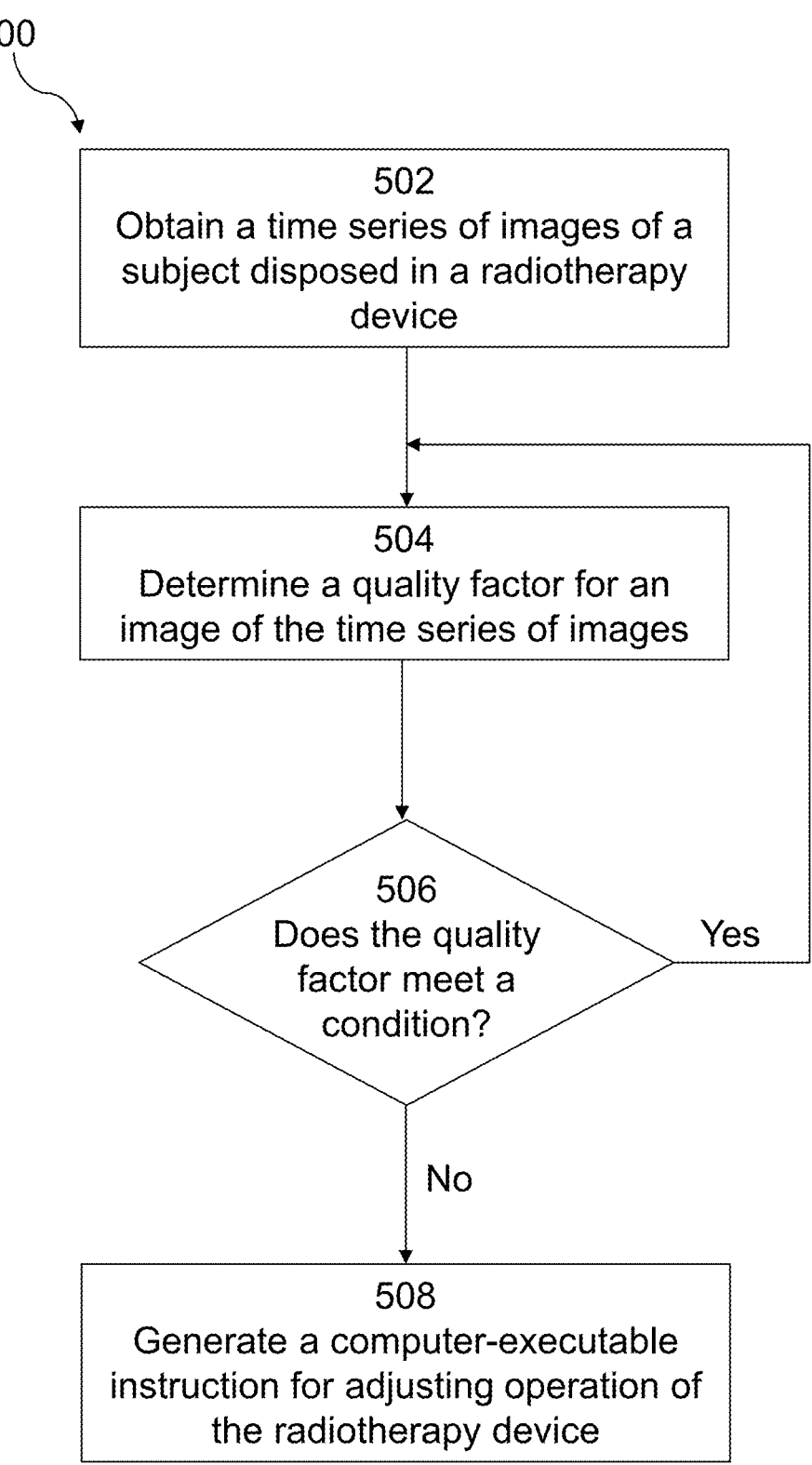
FIG. 5 depicts a computer-implemented image evaluation method according to the present disclosure.

FIG. 5 depicts a computer-implemented image evaluation method according to the present disclosure. The method may be performed, for example, by a radiotherapy device, a controller of a radiotherapy device, or a computer communicatively coupled to a radiotherapy device.

In a step 502, a time series of images of a subject disposed in a radiotherapy device may be obtained. For example, each image of the time series of images may be a 2D MR image or a 2D kV image. The images may alternate between the coronal and sagittal planes.

In a step 504, a quality factor for an image of the time series of images is determined. Determining the quality factor may comprise determining one or more quality metrics each corresponding to a respective property of the image. The quality metrics may be aggregated or combined to determine the quality factor as described herein.

In a step 506, it may be determined whether the quality factor meets a condition. The quality factor may meet the condition if the image is determined to be high quality, and not meet the condition if the image is determined to be low quality. In some examples, the quality factor may meet the condition if all of the quality metrics evaluated indicate that the image is high quality, and may not meet the condition otherwise.

If the quality factor is determined to be meet the condition, the method may return to step 504 to determine a quality factor for another image of the time series of images. Alternatively, the method may return to step 502 to obtain one or more further images, e.g. to extend the time series of images.

If the quality factor is determined not to meet the condition, the method may continue to step 508. In step 508, a computer-executable instruction for adjusting operation of the radiotherapy device may be generated. In some examples, the computer-executable instruction may be configured to stop or prevent application of a radiotherapy beam. The computer-executable instruction may be transmitted to a component of the radiotherapy device, which may implement the computer-executable instruction to adjust or halt radiotherapy treatment.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

Figure 6:
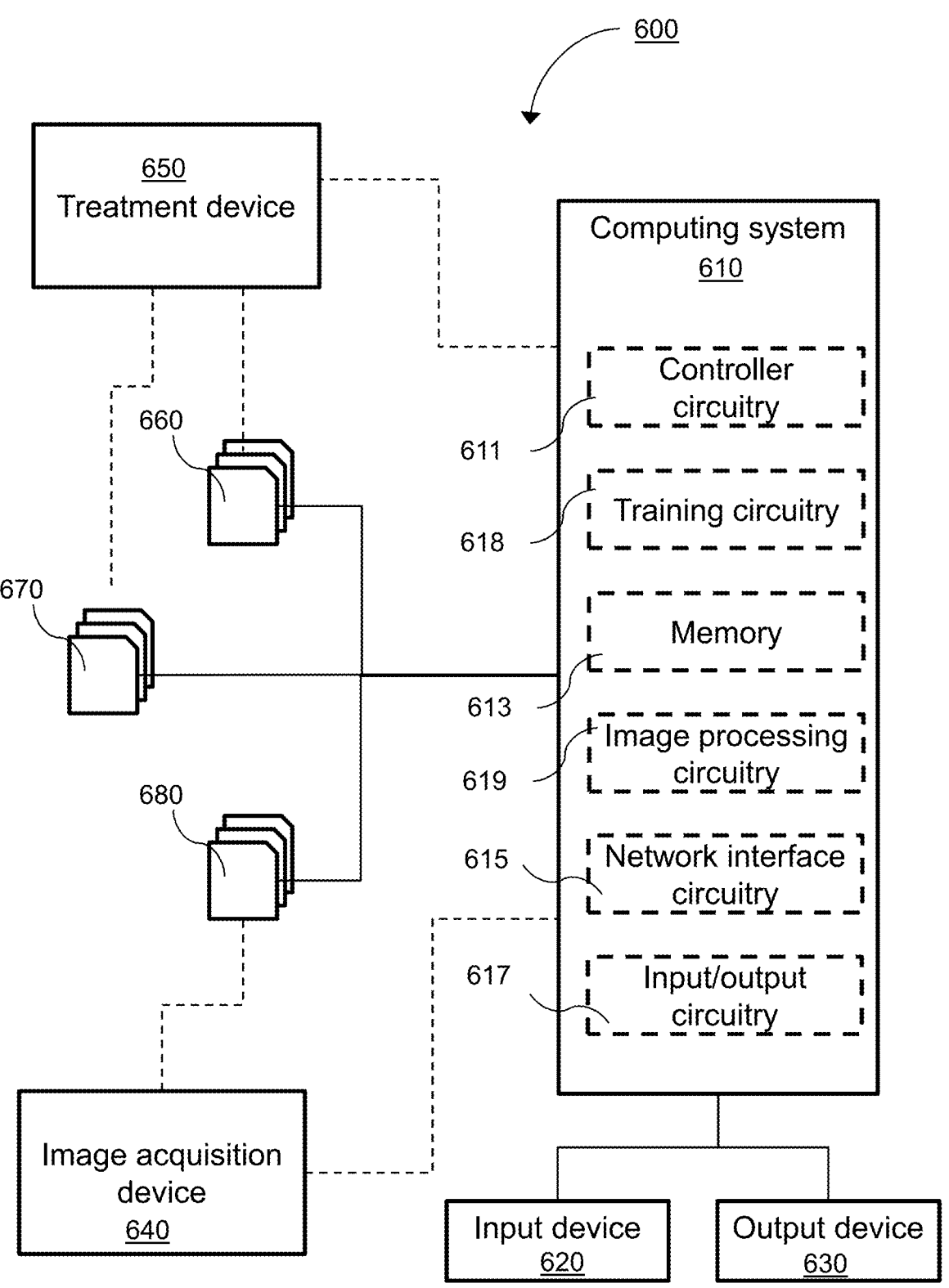
FIG. 6 depicts a block diagram of one implementation of a radiotherapy system according to the present disclosure.

FIG. 6 illustrates a block diagram of one implementation of a radiotherapy system 600. The radiotherapy system 600 comprises a computing system 610 within which a set of instructions, for causing the computing system 610 to perform any one or more of the methods discussed herein, may be executed.

The computing system 610 shall be taken to include any number or collection of machines, e.g. computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 610 includes controller circuitry 611 and a memory 613 (e.g., read-only memory (ROM), flash memory, dynamic random access memory (DRAM) such as synchronous DRAM (SDRAM) or Rambus DRAM (RDRAM), etc.). The memory 613 may comprise a static memory (e.g., flash memory, static random access memory (SRAM), etc.), and/or a secondary memory (e.g., a data storage device), which communicate with each other via a bus (not shown).

Controller circuitry 611 represents one or more general-purpose processors such as a microprocessor, central processing unit, accelerated processing units, or the like. More particularly, the controller circuitry 611 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 611 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 611 is configured to execute the processing logic for performing the operations and steps discussed herein.

The computing system 610 may further include a network interface circuitry 615. The computing system 610 may be communicatively coupled to an input device 620 and/or an output device 630, via input/output circuitry 617. In some implementations, the input device 620 and/or the output device 630 may be elements of the computing system 610. The input device 620 may include an alphanumeric input device (e.g., a keyboard or touchscreen), a cursor control device (e.g., a mouse or touchscreen), an audio device such as a microphone, and/or a haptic input device. The output device 630 may include an audio device such as a speaker, a video display unit (e.g., a liquid crystal display (LCD) or a cathode ray tube (CRT)), and/or a haptic output device. In some implementations, the input device 620 and the output device 630 may be provided as a single device, or as separate devices.

In some implementations, computing system 610 includes training circuitry 618. The training circuitry 618 is configured to train a method of evaluating images and/or a method of detecting large deformations in images. For example, training circuitry 618 may train a model for performing a method of evaluating images/a method of detecting large deformations in images. The model may comprise a deep neural network (DNN), such as a convolutional neural network (CNN) and/or recurrent neural network (RNN). Training circuitry 618 may be configured to execute instructions to train a model that can be used to evaluate images/ detect large deformations in images, as described herein. Training circuitry 618 may be configured to access training data and/or testing data from memory 613 or from a remote data source, for example via network interface circuitry 615. In some examples, training data and/or testing data may be obtained from an external component, such as image acquisition device 640 and/or treatment device 650. In some implementations, training circuitry 618 may be used to update, verify and/or maintain the model for evaluating images/detecting large deformations in images.

In some implementations, the computing system 610 may comprise image processing circuitry 619. Image processing circuitry 619 may be configured to process image data 680 (e.g. images, or imaging data), such as medical images obtained from one or more imaging data sources, a treatment device 650 and/or an image acquisition device 640 as described herein. Image processing circuitry 619 may be configured to process, or pre-process, image data. For example, image processing circuitry 619 may convert received image data into a particular format, size, resolution or the like. In some implementations, image processing circuitry 619 may be combined with controller circuitry 611.

In some implementations, the radiotherapy system 600 may further comprise an image acquisition device 640 and/or a treatment device 650, such as those disclosed herein (e.g. in relation to FIG. 1). The image acquisition device 640 and the treatment device 650 may be provided as a single device. In some implementations, treatment device 650 is configured to perform imaging, for example in addition to providing treatment and/or during treatment. The treatment device 650 comprises the main radiation delivery components of the radiotherapy system described herein.

Image acquisition device 640 may be configured to perform positron emission tomography (PET), computed tomography (CT), magnetic resonance imaging (MRI), etc.

Image acquisition device 640 may be configured to output image data 680, which may be accessed by computing system 610. Treatment device 650 may be configured to output treatment data 660, which may be accessed by computing system 610.

Computing system 610 may be configured to access or obtain treatment data 660, planning data 670 and/or image data 680. Treatment data 660 may be obtained from an internal data source (e.g. from memory 613) or from an external data source, such as treatment device 650 or an external database. Planning data 670 may be obtained from memory 613 and/or from an external source, such as a planning database. Planning data 670 may comprise information obtained from one or more of the image acquisition device 640 and the treatment device 650.

Figure 7:
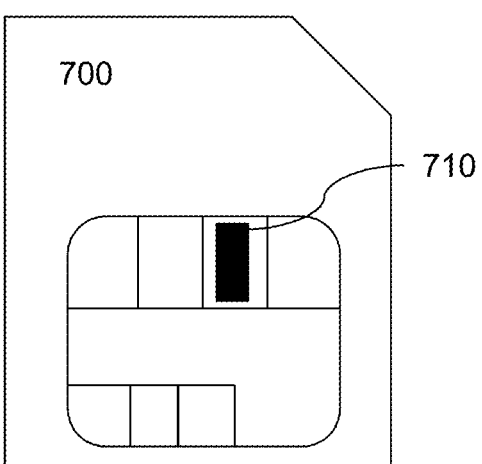
FIG. 7 depicts a computer program product according to the present disclosure.

The various methods described above may be implemented by a computer program. The computer program may include computer code (e.g. instructions) 710 arranged to instruct a computer to perform the functions of one or more of the various methods described above. The steps of the methods described above may be performed in any suitable order. The computer program and/or the code 710 for performing such methods may be provided to an apparatus, such as a computer, on one or more computer readable media or, more generally, a computer program product 700)), depicted in FIG. 7. The computer readable media may be transitory or non-transitory. The one or more computer readable media 700 could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions 710 may also reside, completely or at least partially, within the memory 613 and/or within the controller circuitry 611 during execution thereof by the computing system 610, the memory 613 and the controller circuitry 611 also constituting computer-readable storage media.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASIC. A hardware component may also include programmable logic or circuitry that is temporarily configured by software to perform certain operations.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "obtaining," "detecting," "generating," "aggregating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The disclosure comprises the following items:

1. A computer-implemented image evaluation method for a radiotherapy device, the method comprising:

obtaining a time series of images of a subject disposed in the radiotherapy device;

determining a quality factor for an image of the time series of images; and in response to determining that the quality factor does not meet a condition, generating a computer-executable instruction for adjusting operation of the radiotherapy device.

2. A method according to item 1, wherein determining the quality factor comprises determining one or more quality metrics, each of the quality metrics being associated with a different respective property of the image.

3. A method according to item 2, wherein the one or more quality metrics comprises a plurality of quality metrics, and determining the quality factor comprises aggregating the plurality of quality metrics.

4. A method according to item 2 or item 3, wherein determining the one or more quality metrics comprises determining the amplitude of deformation of anatomical features of the image relative to corresponding anatomical features of a template image.

5. A method according to any of items 2-4, wherein determining the one or more quality metrics comprises determining an amount of jitter associated with a motion tracking estimate for the image relative to respective motion tracking estimates for one or more previous images of the time series of images.

6. A method according to any of items 2-5, wherein determining the one or more quality metrics comprises determining motion of the subject, perpendicular to the image acquisition plane, between the image and one or more other images of the time series of images.

7. A method according to any of items 2-6, wherein determining the one or more quality metrics comprises comparing the image and one or more other images of the time series of images to determine presence or absence of motion of the subject.

8. A method according to any of items 2-7, wherein determining the one or more quality metrics comprises transforming the image with one or more transformations and comparing each transformed image to a template image to detect any change in normalized cross-correlation score in the vicinity of a motion tracking estimate.

9. A method according to any of items 2-8, wherein determining the one or more quality metrics comprises comparing the image intensity of the image and one or more other images of the time series of images to detect global changes in contrast.

10. A method according to any of items 3-9, wherein determining the quality factor comprises selecting the plurality of quality metrics that are aggregated based on a type of treatment indicated in a treatment plan.

11. A method according to any of items 3-10, comprising determining that the quality factor does not meet the condition if any of the aggregated plurality of quality metrics does not meet a subcondition associated with the respective quality metric.

12. A method according to any preceding item, wherein each image of the time series of images is a 2D MR image, or wherein each image of the time series of images is a 2D kV image.

13. A method according to any preceding item, comprising:

determining another quality factor for another image of the time series of images, the another image immediately preceding the image; and in response to determining that the quality factor and/or the another quality factor does not meet the condition, generating the computer-executable instruction for adjusting operation of the radiotherapy device.

14. A method according to any preceding item, wherein the computer-executable instruction is configured to stop or prevent delivery of a radiation beam.

15. A radiotherapy device comprising:
a radiation source configured to apply a radiation beam;
an imaging apparatus; and
a controller communicatively coupled to the radiation source and the imaging apparatus, the controller being configured to:
    obtain a time series of images of a subject disposed in the radiotherapy device;
    determine a quality factor for an image of the time series of images; and
    in response to determining that the quality factor does not meet a condition, generate a computer-executable instruction for adjusting operation of the radiotherapy device.

16. A radiotherapy device according to item 15, wherein the controller being configured to determine the quality factor comprises the controller being configured to determine one or more quality metrics, each of the quality metrics being associated with a different respective property of the image.

17. A radiotherapy device according to item 16, wherein the one or more quality metrics comprises a plurality of quality metrics, and the controller being configured to determine the quality factor comprises the controller being configured to aggregate the plurality of quality metrics.

18. A radiotherapy device according to item 16 or item 17, wherein the controller being configured to determine the one or more quality metrics comprises the controller being configured to:
determine the amplitude of deformation of anatomical features of the image relative to corresponding anatomical features of a template image; and/or
determine an amount of jitter associated with a motion tracking estimate for the image relative to respective motion tracking estimates for one or more previous images of the time series of images; and/or
determine motion of the subject, perpendicular to the image acquisition plane, between the image and one or more other images of the time series of images; and/or
compare the image and one or more other images of the time series of images to determine presence or absence of motion of the subject; and/or
transform the image with one or more transformations and comparing each transformed image to a template image to detect any change in normalized cross-correlation score in the vicinity of a motion tracking estimate; and/or
compare the image intensity of the image and one or more other images of the time series of images to detect global changes in contrast.

19. A radiotherapy device according to item 17 or item 18, wherein the controller being configured to determine the quality factor comprises the controller being configured to select the plurality of quality metrics that are aggregated based on a type of treatment indicated in a treatment plan.

20. A radiotherapy device according to any of items 17-19, comprising the controller being configured to determine that the quality factor does not meet the condition if any of the aggregated plurality of quality metrics does not meet a subcondition associated with the respective quality metric.

21. A radiotherapy device according to any of items 15-20, wherein each image of the time series of images is a 2D MR image, or wherein each image of the time series of images is a 2D kV image.

22. A radiotherapy device according to any of items 15-21, wherein the controller is configured to:
determine another quality factor for another image of the time series of images, the another image immediately preceding the image; and
in response to determining that the quality factor and/or the another quality factor does not meet the condition, generate the computer-executable instruction for adjusting operation of the radiotherapy device.

23. A radiotherapy device according to any of items 15-22, wherein the computer-executable instruction is configured to stop or prevent delivery of a radiation beam.

24. A computer-readable medium storing instructions which, when executed by a processor, cause the processor to perform the method of any of items 1-14.

What is claimed is:

1. A computer-implemented image evaluation method for a radiotherapy device, the method comprising:
    obtaining a time series of images of a subject disposed in the radiotherapy device, wherein at least one of: each image of the time series of images includes a two-dimensional (2D) magnetic resonance (MR) image, or each image of the time series of images includes a 2D kilo voltage (kV) image;
    determining a quality factor for an image of the time series of images; and
    in response to determining that the quality factor does not meet a condition, generating a computer-executable instruction for adjusting operation of the radiotherapy device.

2. The method according to claim 1, wherein determining the quality factor comprises determining one or more quality metrics, each of the one or more quality metrics being associated with a different respective property of the image.

3. The method according to claim 2, wherein the one or more quality metrics comprises a plurality of quality metrics, and determining the quality factor comprises aggregating the plurality of quality metrics.

4. The method according to claim 2, wherein determining the one or more quality metrics comprises determining an amplitude of deformation of anatomical features of the image relative to corresponding anatomical features of a template image.

5. The method according to claim 2, wherein determining the one or more quality metrics comprises determining an amount of jitter associated with a motion tracking estimate for the image relative to respective motion tracking estimates for one or more previous images of the time series of images.

6. The method according to claim 2, wherein determining the one or more quality metrics comprises determining a motion of the subject, perpendicular to an image acquisition plane, between the image and one or more other images of the time series of images.

7. The method according to claim 2, wherein determining the one or more quality metrics comprises comparing the image and one or more other images of the time series of images to determine a presence or an absence of motion of the subject.

8. The method according to claim 2, wherein determining the one or more quality metrics comprises transforming the image with one or more transformations and comparing each transformed image to a template image to detect any change in a normalized cross-correlation score in a vicinity of a motion tracking estimate.

9. The method according to claim 2, wherein determining the one or more quality metrics comprises comparing an image intensity of the image and one or more other images of the time series of images to detect global changes in contrast.

10. The method according to claim 3, wherein determining the quality factor comprises selecting the plurality of quality metrics that are aggregated based on a type of treatment indicated in a treatment plan, and/or the method comprising:

determining that the quality factor does not meet the condition when any of the aggregated plurality of quality metrics does not meet a sub-condition associated with a respective quality metric.

11. The method according to claim 1, comprising:

determining another quality factor for another image of the time series of images, the another image immediately preceding the image; and in response to determining that the quality factor and/or the another quality factor does not meet the condition, generating the computer-executable instruction for adjusting operation of the radiotherapy device.

12. The method according to claim 1, wherein the computer-executable instruction is configured to stop or prevent delivery of a radiation beam.

13. A radiotherapy device comprising:

a radiation source configured to apply a radiation beam;

an imaging apparatus; and a controller communicatively coupled to the radiation source and the imaging apparatus, the controller being configured to:

obtain a time series of images of a subject disposed in the radiotherapy device, wherein at least one of: each image of the time series of images includes a two-dimensional (2D) magnetic resonance (MR) image, or each image of the time series of images includes a 2D kilo voltage (kV) image;

determine a quality factor for an image of the time series of images; and in response to determining that the quality factor does not meet a condition, generate a computer-executable instruction for adjusting operation of the radiotherapy device.

14. The radiotherapy device according to claim 13, wherein the controller being configured to determine the quality factor comprises the controller being configured to determine one or more quality metrics, wherein each of the one or more quality metrics is associated with a different respective property of the image, and wherein the one or more quality metrics comprises a plurality of quality metrics, and wherein the controller being configured to determine the quality factor comprises the controller being configured to aggregate the plurality of quality metrics.

15. The radiotherapy device according to claim 14, wherein the controller being configured to determine the one or more quality metrics comprises the controller being configured to:

determine an amplitude of deformation of anatomical features of the image relative to corresponding anatomical features of a template image;

determine an amount of jitter associated with a motion tracking estimate for the image relative to respective motion tracking estimates for one or more previous images of the time series of images;

determine motion of the subject, perpendicular to an image acquisition plane, between the image and one or more other images of the time series of images;

compare the image and one or more other images of the time series of images to determine presence or absence of motion of the subject;

transform the image with one or more transformations and comparing each transformed image to a template image to detect any change in normalized cross-correlation score in a vicinity of a motion tracking estimate; and/or compare an image intensity of the image and one or more other images of the time series of images to detect global changes in contrast.

16. The radiotherapy device according to claim 14, wherein the controller being configured to determine the quality factor comprises the controller being configured to select the plurality of quality metrics that are aggregated based on a type of treatment indicated in a treatment plan, and/or wherein the controller is configured to determine that the quality factor does not meet the condition when any of the aggregated plurality of quality metrics does not meet a sub-condition associated with a respective quality metric.

17. The radiotherapy device according to claim 13, wherein the computer-executable instruction is configured to stop or prevent delivery of a radiation beam.

18. The radiotherapy device according to claim 13, wherein the controller is configured to:

determine another quality factor for another image of the time series of images, the another image immediately preceding the image; and in response to determining that the quality factor and/or the another quality factor does not meet the condition, generate the computer-executable instruction for adjusting operation of the radiotherapy device.

19. A non-transitory computer-readable medium storing instructions which, when executed by a processor, cause the processor to:

obtain a time series of images of a subject disposed in a radiotherapy device, wherein at least one of: each image of the time series of images includes a two-dimensional (2D) magnetic resonance (MR) image, or each image of the time series of images includes a 2D kilo voltage (kV) image;

determine a quality factor for an image of the time series of images; and in response to determining that the quality factor does not meet a condition, generate a computer-executable instruction for adjusting operation of the radiotherapy device.

* * * * *